＝United States Patent [19]
Yoo et al.

[11] Patent Number: 5,270,039
[45] Date of Patent: Dec. 14, 1993

[54] METHOD FOR SUPPRESSING MYCOTIC INFECTION IN GARLIC AND MICROORGANISMS USED THEREFOR

[75] Inventors: Sung-Joon Yoo; Kiroku Kobayashi; Akira Ogoshi, all of Sapporo; Hiroyuki Sugimoto; Yoshio Kajimura, both of Hiroshima, all of Japan

[73] Assignee: Wakunaga Seiyaku Kabushiki Kaisha, Osaka, Japan

[21] Appl. No.: 788,139

[22] Filed: Nov. 5, 1991

[30] Foreign Application Priority Data

Apr. 30, 1991 [JP] Japan .................................. 3-098670

[51] Int. Cl.$^5$ ........................................... A01N 63/04
[52] U.S. Cl. ................................. 424/93 Q; 435/429; 435/256.5
[58] Field of Search ................. 424/930; 435/254, 929

[56] References Cited
U.S. PATENT DOCUMENTS 4,988,586  1/1991  Toyoda et al. .................... 435/172.1

FOREIGN PATENT DOCUMENTS 1090107  4/1989  Japan ................................. 424/93 Q
1165506  6/1989  Japan ................................. 424/93 Q

*Primary Examiner*—Douglas W. Robinson
*Assistant Examiner*—Jean C. Witz
*Attorney, Agent, or Firm*—Oblon, Spivak, McClelland, Maier & Neustadt

[57] ABSTRACT

Disclosed are the novel microorganisms HF8815 and HF8835 belonging to Genus *Fusarium oxysporum* which are non-pathogenic to garlic and capable of suppressing mycotic infection in garlic. A suppressant for mycotic infection in garlic comprising said microorganisms or its culture medium as an effective ingredient and a method for suppressing mycotic infection in garlic utilizing said suppressant are also disclosed. The use of the microorganism can effectively suppress the mycotic infection in garlic effectuating a biological means involving cross defense mechanism without giving any adverse effects to the soil nor deteriorating the environment.

3 Claims, 4 Drawing Sheets

METHOD FOR SUPPRESSING MYCOTIC INFECTION IN GARLIC AND MICROORGANISMS USED THEREFOR

BACKGROUND OF THE INVENTION

1. Field of the Invention

The present invention relates to a method for suppressing mycotic infection in garlic, and, more particularly, to a cross defense method for suppressing mycotic infection in garlic such as garlic dry-rot, and to microorganisms used for said cross defense method.

2. Description of the Background Art

In the modern agriculture, the excessive pursuit of profit has expelled its long cherished crop rotation system and forced the agricultural system into repeated cultivation or exclusive cultivation of the same crop on the same ground. In addition, the repeated use of abundant chemical fertilizers, soil improvers and herbicides for maintaining this crop system eventually lead to the outbreak of unforeseeable soil diseases in many crop fields. A major cause of the diseases is considered to be the increase in the population of pathogens in the soil. Although various germicides have been used as a countermeasure to this problem, they sometimes worked adversely to kill even useful microorganisms so that they worsen the soil conditions than ever and not necessarily deemed as an effective measure. Risks to the environment caused by the abundant use of chemicals, including germicides or the like, are also pointed out.

Under these circumstances, interest in the biological fungicides, that are microorganisms which suppress harmful creatures, is increasing. This kind of suppressing measure, which involves cross defense mechanism, is advantageous in that it attacks only specific creatures and not contaminates the surrounding environment. Among a number of researches on biological fungicides in the past, there is a report that the use of a non-pathogenic strain of *Fusarium oxysporum* isolated from the roots of sweet potato was dramatically effective for suppressing the stem-rot of sweet potatoes (Ogawa et al. Syokubutsu boueki, vol.38, No.12, pp.535-538, 1984). Regrettably, the suppressing effect is strictly specific to a certain specie and not directly applicable to other species of plants.

Referring to the diseases of garlic, on the other hand, garlic dry-rot and the like are known as diseases caused by mycotic infection and a method for exterminating these diseases has been earnestly desired.

The present invention is, therefore, directed to the provision of a novel microorganism effective in the suppression of mycotic infection in garlic and to a method for exterminating the diseases in garlic by the use of such a microorganism.

In view of this situation, the inventors of the present invention have conducted extensive studies, and as a result, have succeeded in the isolation of novel fungi from a healthy bulb of a garlic or the rhizosphere of garlic roots and found that the fungi possessed a cross defense ability against mycotic infection in garlic. This finding has led to the completion of the present invention.

SUMMARY OF THE INVENTION

Accordingly, an object of the present invention is to provide a microorganism belonging to Genus *Fusarium oxysporum*, which is non-pathogenic to garlic and capable of suppressing mycotic infection in garlic.

As specific embodiments, the present invention provides microorganisms isolated from the surface or tissue of garlic roots or from their rhizosphere, and identified and designated as *Fusarium oxysporum* HF8815 (Depositary No: FERM P-12218) and *Fusarium oxysporum* HF8835 (Depositary No: FERM P-12217).

Another object of the present invention is to provide an antimycotic agent comprising said microorganism or its culture medium as an effective ingredient.

Still another object of the present invention is to provide a method for suppressing mycotic infection in garlic which comprises applying said microorganism or its culture medium to the cloves, bulbs, roots, or seeds of garlic, or their rhizosphere soil.

Other objects, features and advantages of the invention will become more readily apparent from the following description.

DETAILED DESCRIPTION OF THE INVENTION AND PREFERRED EMBODIMENTS

Figure 1:
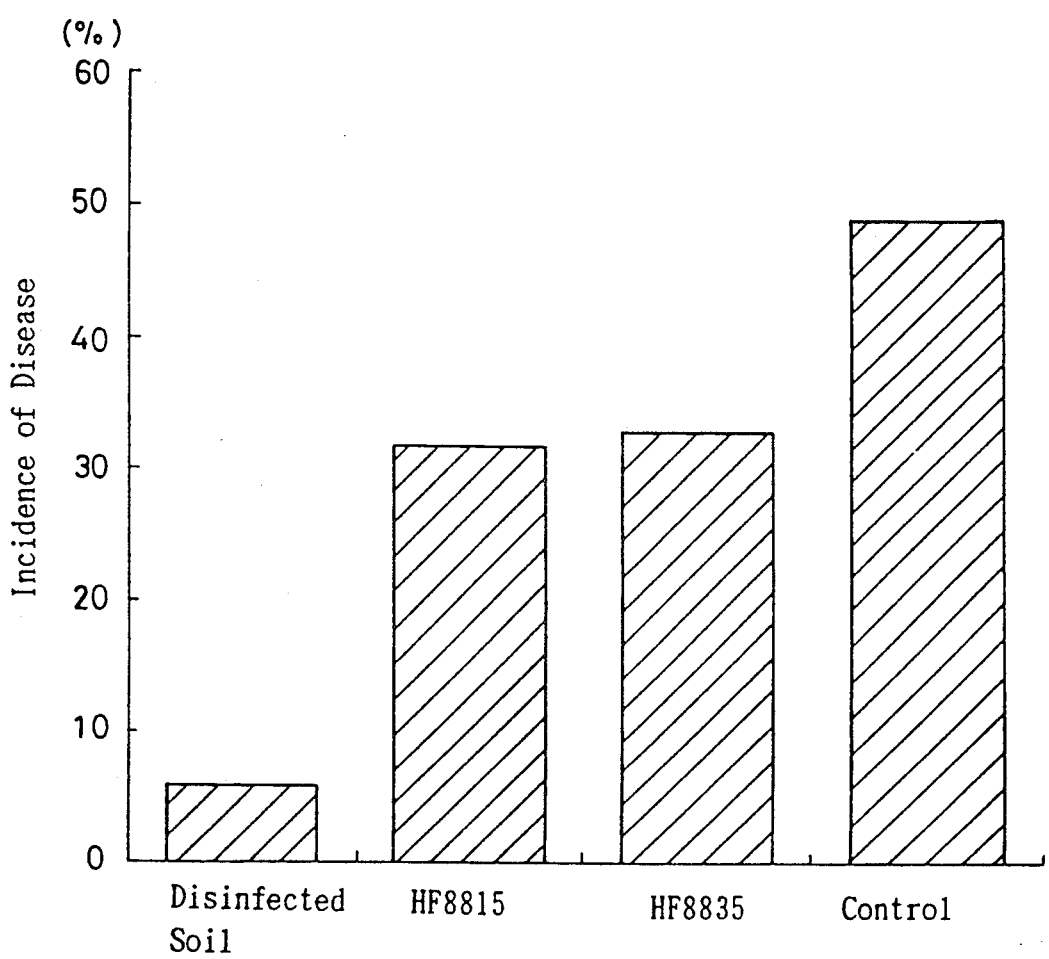
FIG. 1 shows the incidence of disease by pathogenic fungus HF8801 when the microorganisms of the present invention were used, wherein the incidence of disease (%) is taken along the ordinate and the Experimental plots along the abscissa.

The microorganisms of the present invention can be obtained, for example, by collecting the non-pathogenic microorganisms from the roots or tissues of garlic roots, or the rhizosphere of garlic roots. More specifically, they can be collected by first cultivating the tissues or the like of a garlic in an appropriate medium, then inoculating the cultured strains into a soil, followed by planting the cloves, bulbs or seeds on the soil and inspecting the engender of disease of the plant, and isolating the strains free from engender of the disease.

Typical examples of such microorganisms are HF8815 strain and HF8835 strain. Their mycological characteristics are as follows.

(A) MORPHOLOGY AND GROWTH ON VARIOUS CULTURE MEDIA (1) HF8815 Strain

The colonies on the malt extract agar medium spread over the whole surface of a 9 cm petri dish for 7 days at 25° C. A sheer of silk-like mycelia covers the agar surface. The colonies have a color of dull red violet to red violet. The down-like aerial mycelia are found at some places on the surface. The reverse side of colonies is colorless.

The colonies on the potato-sucrose agar medium spread over the whole surface of a 9 cm petri dish for 7 days at 25° C. A sheer of silk-like mycelia covers the agar surface. The down-like aerial mycelia are found at some places on the surface. The colonies have a color of light violet to light reddish violet. The reverse side of colonies is colorless.

(2) HF8835 Strain

The colonies on the malt extract agar medium spread over the surface of a 9 cm petri dish for 7 days at 25° C. The down-like aerial mycelia spread over the surface. The colonies have a color of light violet to violet. Some violet streaks are found on the reverse side of colonies.

The colonies on the potato-sucrose agar medium spread over the surface of a 9 cm petri dish for 7 days at 25° C. The colonies are composed of thin, down-like, violet aerial mycelia. The reverse side of colonies is colorless.

(3) Microconidia (size: 5.0–13.8×2.5–5.0 $\mu$m) of pseudecephalus-shaped are formed in both strains on the phialides extending from mycelia. The chlamydospores (6.2–9.3 $\mu$m) are of circular or oval-shaped and colorless or light brown in color. They have a thick sporoderm with smooth or rough surface. The fungi are acrogenous or intersexual. Macroconidia are of 1–5 dissepiments, colorless, and have a somewhat distorted crescent shape. Many macroconidia having 1–3 dissepiments are formed on monophialides but those having 4–5 dissepiments are few. The size of single dissepiment conidium is 8.8–18.8×2.5–5.0 $\mu$m and that of 3-dissepiments is 17.5–31.3×3.8–5.0 $\mu$m.

(B) PHYSIOLOGICAL CHARACTERISTICS

The optimal temperature for growth on PDA medium was 25°–30° C. for both microorganisms. The pH tests on PDA medium revealed that the both microorganisms could grow in the range of pH 3–10. HF8835 strain grew with greater proliferation in the range of pH 5–7 and HF8815 strain at around pH 4. HF8815 strain excreted a water-soluble pigment of wine red only at pH 3, whereas HF8835 strain excreted no water-soluble pigments at any pH in the range of pH 3–10.

From the observations of foregoing mycological characteristics, particularly from the color of colonies and the morphology of conidispores, both HF8815 and HF8835 strains were concluded to be novel microorganisms belonging to Genus *Fusarium oxysporum*, even though some difference in the amount of aerial mycelia were observed. These microorganisms were named *Fusarium oxysporum* HF8815 and *Fusarium oxysporum* HF8835, and were deposited with the Fermentation Research Institute, Agency of Industrial Science and Technology, Japan with Depositary No. 12218 (FERM P-12217) and No.12217 (FERM P-12218), respectively.

Cultivation of the microorganisms of the present invention can be carried out under normal conditions conventionally employed for the cultivation of microorganisms of Genus Fusarium. PDA medium, Czapek's medium, and the like can be used as a culture medium. Various carbon sources, nitrogen sources, inorganic salts, and the like may be added to the medium. Examples of the carbon sources include saccharides, fatty acids, and the like; nitrogen sources include inorganic nitrogen such as nitrates, ammonium salts, and organic nitrogen such as amino compounds and the like; and inorganic salts include phosphates, sulfates, chlorides, and the like. Other nutrients such as corn steep liquor, yeast extract, and the like can also be added. The appropriate culture temperature is 10°–40° C., preferably around 28° C., and the appropriate culture pH is 4–8, preferably around 6.5.

Since the microorganisms of the present invention are non-pathogenic to garlic and suppress the mycotic infection in garlic, the application of the microorganisms or its culture media to the cloves, bulbs, roots, seeds and/or rhizosphere soil of garlic can effectively inhibit the mycotic infection in garlic.

In the application of the microorganisms of the present invention or their culture media, either cloves, roots, seeds or the like of garlic, or soils in which they are planted, may be treated with said microorganisms or the culture media. When cloves, roots, seeds or the like of garlic are treated, they are dipped into the suspension liquid of said microorganisms or its culture media and then planted in the field. When soils are to be treated, the soils may be first treated with said microorganisms or the culture media before planting the cloves or the like of garlic, or may be sprayed over the rhizosphere of garlic already set out on the field.

When said microorganisms or their culture media are to be applied to garlic, other components besides said microorganisms, for example, plant growth regulators, saccharides, amino acids, organic acids, alcohols, vitamins, minerals, and the like can optionally be added to said microorganisms or their culture media. There are no limitations to the form of preparations; they may be powders, grains, liquids, and the like.

There are no limitations as to the kind of diseases and injuries of garlic to which the microorganisms of the present invention are applied, insofar as the diseases are ascribable to mycotic infection in garlic. The dry-rot of garlic is a typical example of such a disease.

Consequently, the use of microorganisms of the present invention can effectively suppress the mycotic infection in garlic by a biological method, which involves the cross defense mechanism, without giving any adverse effects to the soil and without deteriorating the environment.

Other features of the invention will become apparent in the course of the following description of the exemplary embodiments which are given for illustration of the invention and are not intended to be limiting thereof.

EXAMPLES

Example 1

[Isolation of non-pathogenic fungi from healthy root-tissues of garlic or from rhizosphere soil]

A browny-discolored part of a garlic clove was taken off and its surface was sterilized with a solution of sodium hypochlorite (effective chlorine: 0.25%) for 30 minutes. The sterilized specimen of the clove was placed on a wet filter-paper in a petri dish for the culture at 25° C. The microorganisms grew up on the tissue were transplanted and cultured on a Komada's Fusarium selective medium ($K_2HPO_4$ 1 gm, KCl 0.5 gm, $MgSO_4 \cdot 7H_2O$ 0.5 gm, Fe-EDTA 0.01 gm, L-asparagine 2 gm, D-galactose 20 gm, agar 15 gm, water 1000 ml).

The fungi of Genus Fusarium isolated from the medium were further cultured on a Czapek's medium ($NaNO_3$ 3 gm, $K_2HPO_4$ 1 gm, $MgSO_4 \cdot 7H_2O$ 0.5 gm, KCl 0.5 gm, $Fe-SO_4 \cdot 7H_2O$ 0.5 gm, glucose 30 gm, water 1000 ml) and inoculated into a soil. The cloves or sprouts of garlic were planted on the soil to observe the incidence of diseases.

The non-pathogenic strains of HF8815 and HF8835 were thus obtained.

Example 2

[Cultivation of the isolated microorganisms]

The strains of HF8815 and HF8835 prepared and isolated in Example 1 were shake-cultured on Czapek's medium ($NaNO_3$ 3 gm, $K_2HPO_4$ 1 gm, $MgSO_4 \cdot 7H_2O$ 0.5 gm, KCl 0.5 gm, $Fe\text{-}SO_4 \cdot 7H_2O$ 0.5 gm, dextrose 30 gm, water 1000 ml) and the cultured cells were collected by centrifugal sedimentation.

Example 3

[Garlic dry-rot disease suppression test]

(1) Method

Microorganism strains to be tested:
 (a) Garlic dry-rot microorganisms HF8801 and HF8861 (Disclosed by Ogoshi et al. at the symposium of Japan Plant Pathology Association, Hokkaido Branch, November 1990)
 (b) Non-pathogenic garlic dry-rot microorganisms HF8815 and HF8835

Garlic to be tested: Healthy white bulbs

Test fields:

Experimental plots were prepared by inoculating the garlic dry-rot microorganisms HF8801 and HF8861, which had been cultured in advance on a wheat bran soil (25° C., 10 days), in an amount of 5 gm/clove.

A control plot was prepared by sterilizing the field with a soil fumigant (NCS).

Method of inoculation:

250 ml of Czapek's liquid medium was poured into 500 ml shaking flasks and pasteurized. Non-pathogenic Fusarium HF8815 and HF8835 were inoculated onto the media and then cultured for 10 days at 28° C. using a heat-controlled shake-culture apparatus at 110 rpm.

The cultured broth was filtered twice with a folded gauze to eliminate the mycelia and cells were collected by centrifugal sedimentation. Water was added to this sediment to prepare a suspension of spores ($10^6$–$10^7$/ml). The cloves were immersed in this suspension for 15 minutes and then planted on the field. After plantation, the cloves were observed for 10 months. Untreated cloves were planted on the control plot.

Inspection Items:
 (a) Height of plant (cm)
 (b) Weight of bulb (gm)
 (c) Degree of incidence: The incidence of disease was determined according to the following standards.
  0: (healthy) No diseases were found on the leaves.
  1: (0–25%) The disease; yellow discoloration or yellow mottles, were found on $\frac{1}{4}$ of the leaves.
  2: (25–50%) The disease was observed on about $\frac{1}{2}$ of the leaves.
  3: (50–75%) The disease was observed on most of the leaves.
  4: (75–100%) Significant dwarfs or blights were observed.

$$\frac{\Sigma f (\text{Class value}) \times (\text{number of stumps})}{4N} \times 100 = \text{incidence of disease}$$

Class value: 0 and 1, 2, 3, 4
Inspected number of stumps: $N$ (2) Results

Figure 2:
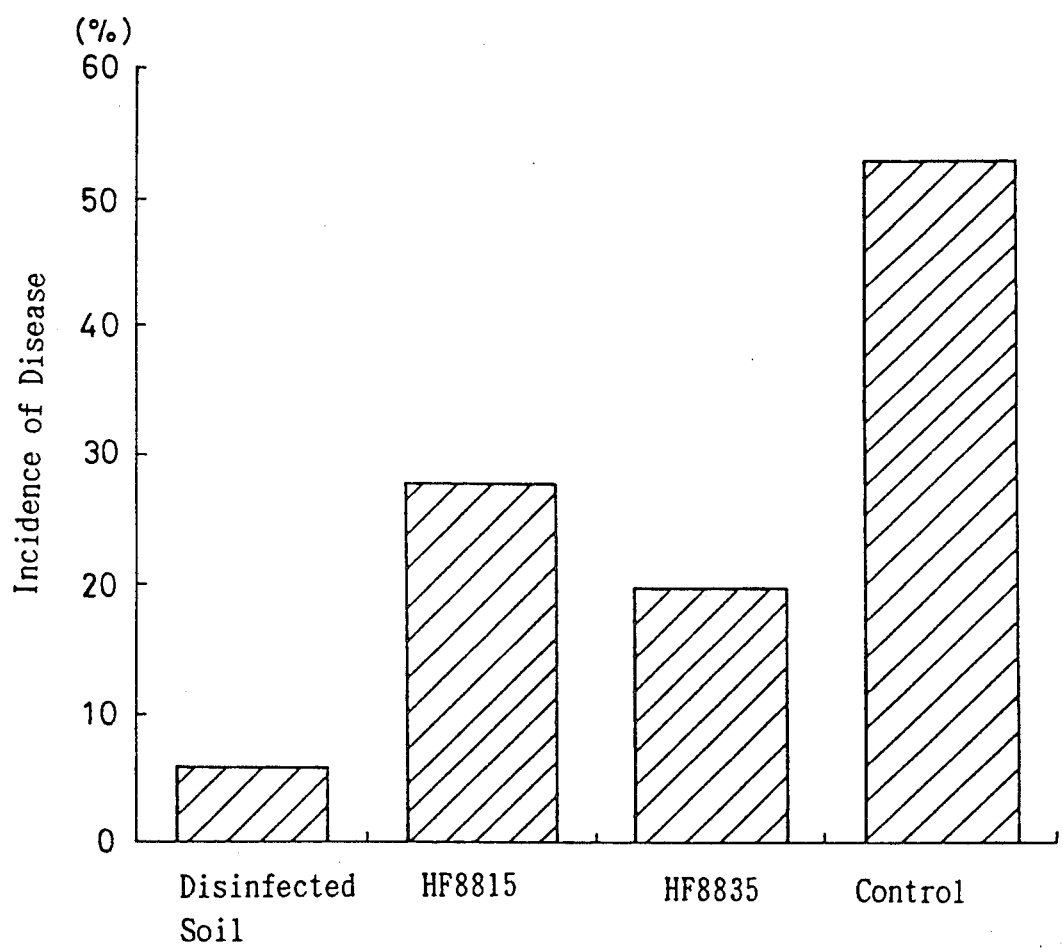
FIG. 2 shows the incidence of the disease by pathogenic fungus HF8861 when the microorganisms of the present invention were used, wherein the incidence of disease (%) is taken along the ordinate and the Experimental plots along the abscissa.
Figure 3:
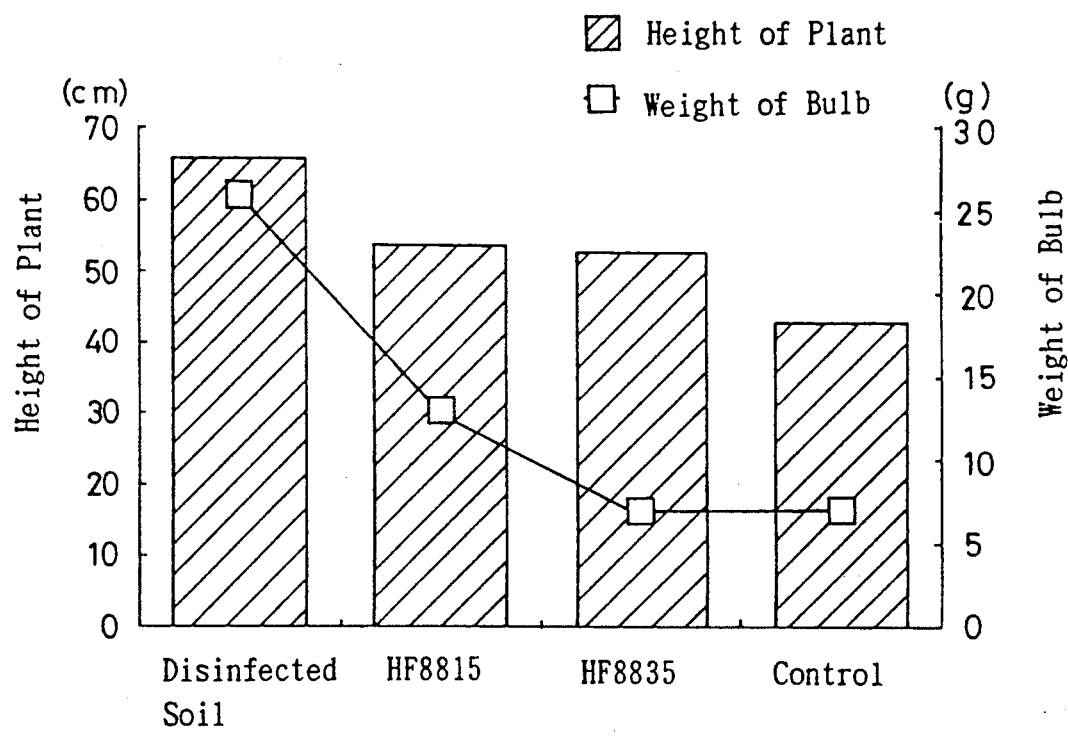
FIG. 3 shows the exterminating effect of the microorganisms of the present invention against pathogenic fungus HF8801, wherein the height of plants (cm) and weight of bulb (gm) are plotted along the ordinates and the Experimental plots along the abscissa.
Figure 4:
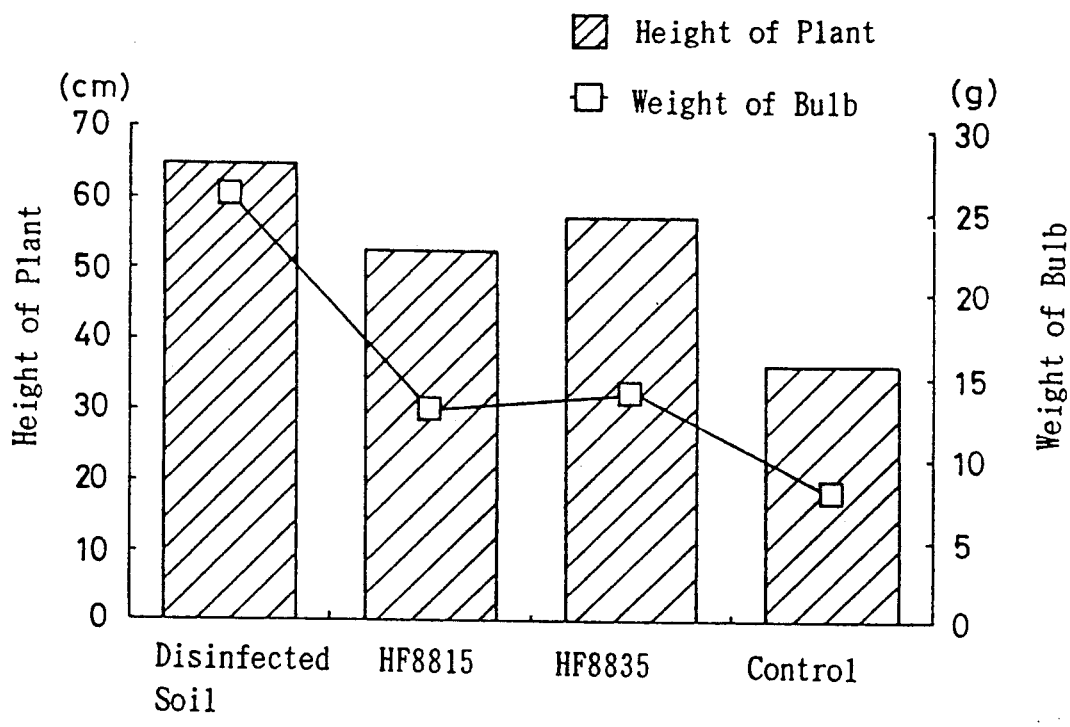
FIG. 4 shows the exterminating effect of the microorganisms of the present invention against pathogenic fungus HF8861, wherein the height of plants (cm) and weight of bulb (gm) are plotted along the ordinates and the Experimental plots along the abscissa.

The incidence of the disease in the control plot was approximately 50% whereas that of the experimental plots treated with HF8815 and HF8835 was approximately 20–30%. The height and weight of the garlics were almost proportionate to the incidence of the disease as shown in FIGS. 1–4.

Obviously, numerous modifications and variations of the present invention are possible in light of the above teachings. It is therefore to be understood that within the scope of the appended claims, the invention may be practiced otherwise than as specifically described herein.

What is claimed is:

1. A method for suppressing mycotic infection in garlic, comprising applying an effective amount of an antimycotic agent comprising a substantially pure microorganism of the species *Fusarium oxysporum* HF8815 (FERM P-12218) or *Fusarium oxysporum* HF8835 (FERM P-12217) to cloves, roots, bulbs, seeds or rhizospheres of garlic, wherein said microorganism is non-pathogenic to garlic and suppresses mycotic infection in garlic.

2. A substantially pure microorganism of *Fusarium oxysporum* HF8815 (FERM P-12218) or *Fusarium oxysporum* HF8835 (FERM P-12217).

3. An antimycotic agent, comprising an amount of microorganism of claim 2 effective to suppress mycotic infection in garlic in combination with a suitable carrier.

* * * * *